(12) United States Patent  (10) Patent No.: US 7,291,148 B2
Agee et al.                 (45) Date of Patent:     Nov. 6, 2007

(54) EXTERNAL FIXATOR FOR COLLES' FRACTURE

(75) Inventors: John M. Agee, Cameron Park, CA (US); Francis C. King, Carmichael, CA (US)

(73) Assignee: John M. Agee Trustee of the John M. Agee Trust, Sacramento, CA (US)

( * ) Notice: Subject to any disclaimer, the term of this patent is extended or adjusted under 35 U.S.C. 154(b) by 515 days.

(21) Appl. No.: 10/454,758

(22) Filed: Jun. 3, 2003

(65) Prior Publication Data

US 2004/0249375 A1    Dec. 9, 2004

(51) Int. Cl.
*A61B 17/00* (2006.01)
*A61F 4/00* (2006.01)

(52) U.S. Cl. ..................................... 606/54

(58) Field of Classification Search ................ 606/54, 606/59, 57, 58
See application file for complete search history.

(56) References Cited

U.S. PATENT DOCUMENTS

| 2,250,417 | A | * | 7/1941 | Ettinger ........................ 606/59 |
| 3,961,854 | A | | 6/1976 | Jaquet |
| 4,548,199 | A | | 10/1985 | Agee |
| 4,554,915 | A | | 11/1985 | Brumfield |
| 4,611,586 | A | | 9/1986 | Agee et al. |
| 4,621,627 | A | | 11/1986 | DeBastiani et al. |
| 4,628,919 | A | | 12/1986 | Clyburn |
| 4,922,896 | A | | 5/1990 | Agee et al. |
| 4,988,349 | A | | 1/1991 | Pennig |
| 5,122,140 | A | * | 6/1992 | Asche et al. .................. 606/55 |
| 5,152,280 | A | | 10/1992 | Danieli |
| 5,207,676 | A | * | 5/1993 | Canadell et al. ............... 606/54 |
| RE34,985 | E | | 6/1995 | Pennig |
| 5,437,666 | A | | 8/1995 | Tepic et al. |
| 5,437,667 | A | | 8/1995 | Papierski et al. |
| 5,451,226 | A | * | 9/1995 | Pfeil et al. ..................... 606/59 |
| 5,545,162 | A | | 8/1996 | Huebner |
| 5,620,442 | A | | 4/1997 | Bailey et al. |
| 5,662,649 | A | | 9/1997 | Huebner |
| 5,683,389 | A | | 11/1997 | Orsak |
| 5,743,898 | A | | 4/1998 | Bailey et al. |
| 5,769,851 | A | | 6/1998 | Veith |
| 5,897,555 | A | * | 4/1999 | Clyburn et al. ............... 606/54 |
| 6,001,097 | A | | 12/1999 | Campopiano et al. |
| 6,010,510 | A | | 1/2000 | Raskin et al. |
| 6,080,153 | A | | 6/2000 | Mata et al. |

(Continued)

FOREIGN PATENT DOCUMENTS

EP    0397059 A2    11/1990

(Continued)

*Primary Examiner*—Anuradha Ramana
(74) *Attorney, Agent, or Firm*—Townsend and Townsend and Crew LLP; Henry Heines

(57) ABSTRACT

Bone fragments resulting from a Colles' fracture of the distal radius bone are set in position by an external fixator that includes mounting structures attachable to the radius at a site proximal to the fracture and to a metacarpal, joined by a connector whose length is capable of both gross adjustment and precision adjustment, each mounting structure providing degrees of freedom independently of the connector length, the mounting structure at the radius end providing independent degrees of freedom for rotation around a proximal-distal axis and for rotation about an axis transverse to an axis parallel to the proximal-distal axis.

13 Claims, 13 Drawing Sheets

U.S. PATENT DOCUMENTS

| | | |
|---|---|---|
| 6,162,223 A | 12/2000 | Orsak et al. |
| 6,162,224 A | 12/2000 | Huebner |
| 6,171,309 B1 | 1/2001 | Huebner |
| 6,217,577 B1 * | 4/2001 | Hofmann ..................... 606/57 |
| 6,245,071 B1 | 6/2001 | Pierson |
| 6,409,729 B1 | 6/2002 | Martinelli et al. |
| 6,428,540 B1 | 8/2002 | Claes et al. |
| 6,491,694 B1 * | 12/2002 | Orsak .......................... 606/57 |

FOREIGN PATENT DOCUMENTS

| | | |
|---|---|---|
| EP | 0420430 A1 | 4/1991 |
| FR | 2805147 A1 | 8/2001 |
| WO | WO 91/11149 * | 8/1991 |
| WO | WO 99/22661 A1 | 5/1999 |
| WO | WO 01/91654 A1 | 12/2001 |
| WO | WO 01/91655 A1 | 12/2001 |
| WO | WO 02/069816 A2 | 9/2002 |

* cited by examiner

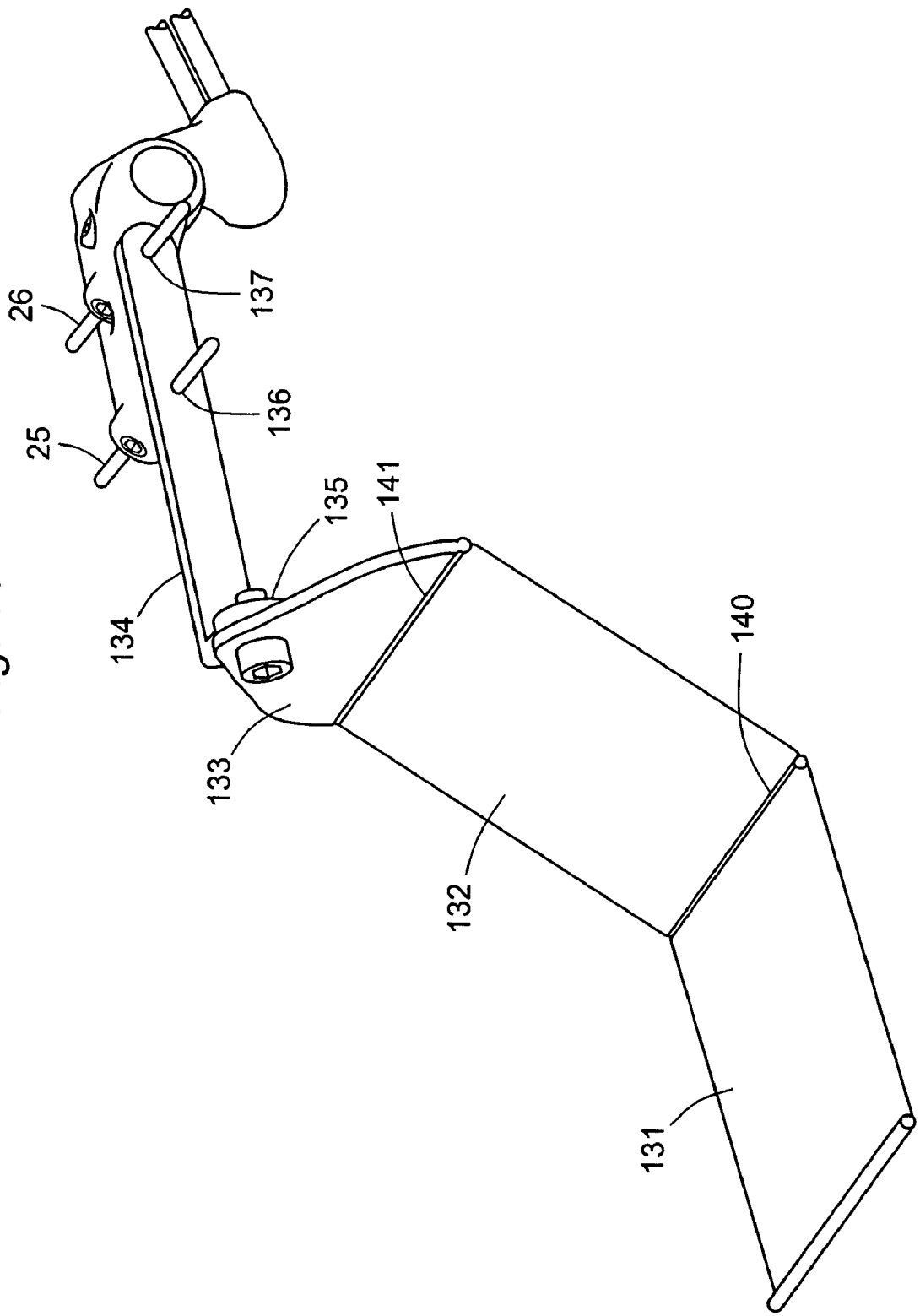

EXTERNAL FIXATOR FOR COLLES' FRACTURE

BACKGROUND OF THE INVENTION

1. Field of the Invention

This invention resides in the field of external fixators, which are medical devices that serve as splints to treat fractures of long bones in general and specifically the forearm and distal radius.

2. Description of the Prior Art

Colles' fractures are a common injury among adults, including middle-aged to elderly women who suffer from osteoporosis as well as younger adults who suffer falls during sports or other vigorous activities. A Colles' fracture is a fracture of the radius, i.e., the forearm bone on the thumb side. The fracture typically occurs when one begins to fall and extends one's hand as a reflex to lessen the force of hitting the ground. The fall produces a sudden impact of the body weight on the heel of the hand which results in a fracture of the radius just above the wrist joint with or without an associated wrist joint injury.

The realignment and setting of bones crushed by a Colles' fracture are typically performed with the aid of an external fixator or fixation device, which is a mechanically adjustable splint that is mounted externally to the forearm and hand through percutaneous pins or screws that secure the device to the bones on either side of the fracture site. External fixators are designed to permit initial alignment of the fracture fragments and then stabilize the fragments and injured soft tissue as they heal.

Alignment of the bone fragments is a complex task in view of the numerous degrees of freedom in the region of the forearm, wrist and hand. The typical fracture causes misalignment of the fragments both rotationally and translationally with respect to a conventional set of orthogonal anatomical axes of the forearm, wrist and hand. Translational misalignment can occur for example in the radial-ulnar, palmar-dorsal, and proximal-distal directions, while rotational misalignment can occur about the longitudinal axis of the radius. All of these misalignments must be corrected before the final securement of the fixator. The optimal fixator would be one that contains and effectively integrates all the degrees of freedom necessary to achieve accurate translational and rotational alignment of the fracture efficiently. This is difficult to achieve—the typical fixator of the prior art is incapable of effectively integrating all of these degrees of freedom.

Theoretically, proper alignment of the fracture about the longitudinal axis of the radius could be achieved by proper placement of the fixation pins in the bone. Thus, with a distal set of pins in the stable (index and long finger) metacarpals, a proximal set in the radius at a site proximal to the fracture, and both sets mounted to a fixator, alignment might be achievable when a distraction force is applied between the distal and proximal pins if the pins were inserted in the correct orientation within the plane defined by the stable metacarpals. Achieving this desired orientation of the distal pins is relatively easy, but proper orientation of the proximal pins is considerably more difficult. Numerous fixators and fixator features have been designed to address this difficulty. Even if rotational alignment is achieved, the remaining degrees of freedom used for translational alignment of the fracture are no longer referenced to the conventional set of orthogonal anatomical axes of the forearm, wrist and hand (i.e., those axes that are recognized as a frame of reference among surgeons who specialize in these fractures). Consequently, when adjustments are made to align the fracture translationally, the procedure suffers from three disadvantages. First, translation of the fracture fragments has not been achieved along the conventional anatomical axes. Second, adjustment along a single axis cannot be performed without affecting translation of the fracture along the other two axes. Both of these disadvantages make it difficult for the surgeon to correlate adjustments made to the fixator with x-ray images taken after the adjustment. The third disadvantage is that once all adjustments to the fracture have been made, the flexion-extension axis about which the fixator can rotate is fixed relative to the anatomical flexion-extension axis of the wrist joint. If these axes are not substantially colinear, any wrist flexion or extension will cause misalignment of the fracture.

What is therefore needed is a fixator that enables the surgeon to achieve rotational alignment of the fracture along the longitudinal axis of the radius, even when the proximal pins are inserted in an incorrect orientation (i.e., the pins are not all in a common plane when the fracture is rotationally aligned), and still retain the correct reference between the fixator translational degrees of freedom and the orthogonal anatomical axes of the forearm, wrist and hand.

SUMMARY OF THE INVENTION

These interests are served by the present invention, which resides in an external fixator that, after having been secured to the metacarpal(s) and the radius, provides all degrees of freedom necessary to achieve both rotational alignment and gross translational alignment of the fracture. Rotational alignment, which is difficult to achieve as well as to confirm by x-ray or by physical exam, is frequently best achieved by manual manipulation of the fracture by the surgeon, a procedure known in the art as "closed reduction." This procedure makes use of the soft tissues of the forearm, wrist, and hand to help move the fractured bone fragments back into proper rotational alignment. Closed reduction also produces gross translational alignment of the fracture fragments. For closed reduction to work appropriately with a fixator attached, the fixator must have certain degrees of freedom that move freely with minimal friction and impose no clinically significant constraints on movement of the fracture.

To enable unconstrained movement of the fracture, the fixator must therefore have several degrees of freedom, as described below. It is essential that these degrees of freedom be referenced to the conventional anatomic axes illustrated in FIG. 1. These axes are the proximal-distal axis x, the radial-ulnar axis y, the palmar-dorsal axis z, and the wrist joint flexion-extension axis w. The radial-ulnary axis is transverse to the plane of the Figure and within the plane formed by the stable finger metacarpals when the wrist is in a neutral position. The proximal-distal axis x is in the plane of the Figure and along the longitudinal axis of the radius. The palmar-dorsal axis z is in the plane of the Figure and orthogonal to the proximal-distal axis x and the radial-ulnar axis y. The degrees of freedom are as follows:

(1) Rotation about an axis which is substantially parallel to the longitudinal axis of the radius and therefore parallel to the x axis, (2) Rotation about an axis that is substantially perpendicular to the longitudinal axis of the radius and generally coincident with the plane defined by the stable finger metacarpals of the hand with the wrist in a neutral position—i.e., this rotation axis of the fixator is substantially parallel to the y axis and when located proximal to the fracture provides arcuate motion that produces translation in the palmar-dorsal direction at the distal end of the fixator, (3) Translation along an axis that is substantially parallel to axis x, the longitudinal axis of the radius, thereby allowing the distal fracture fragments of the radius to move freely in the proximal-distal direction with respect to the proximal shaft of the radius, (4) Translation along an axis that is substantially parallel to axis y which is perpendicular to the longitudinal axis of the radius and generally within the plane defined by the stable finger metacarpals of the hand when the wrist is in a neutral position, thereby allowing the fixator to move the hand, wrist, and distal fracture fragments freely in a radial-ulnar direction, and (5) Rotation about an axis that is substantially co-linear with the anatomical flexion-extension axis w of the wrist joint and ideally passing through the head of the capitate, thereby allowing the hand and wrist to move freely in the direction indicated by the arrow 11 without affecting the fracture alignment.

Note that axes x, y, and z pass through the fracture site (in the radius) while axis w passes through the wrist joint.

Once the desired rotational and gross translational alignments of the fractured bone fragments are achieved using closed reduction, the fixator of this invention can be locked relative to each of these five degrees of freedom, i.e., its components can be immobilized such that the fixator is no longer able to freely rotate or translate in any direction. In preferred embodiments of the invention, the fixator also allows the surgeon to perform incremental adjustments to achieve more accurate alignment on a smaller scale while maintaining the gross alignment achieved during the closed reduction. These incremental adjustments therefore allow the surgeon to make small changes in the translation alignment of the fracture without allowing the fixator to freely rotate or to translate in any other direction. The fixator is designed such that these incremental adjustments are made along the three recognized anatomical axes shown in FIG. 1. In further preferred embodiments, the external fixator provides a movement capability that remains after all adjustments have been made and the desired alignment of the fracture has been achieved. This movement capability is a rotational degree of freedom that is generally coaxial with the flexion-extension rotation axis of the wrist and thereby allows positioning of the hand to avoid both hand stiffness and carpal tunnel syndrome.

This invention thus resides in an external fixation device that includes a structure for mounting to one or more metacarpals, a structure for mounting to a radius, and a connector joining the two mounting structures in a manner that permits them to be moved toward or away from each other by simply pushing them together or pulling them apart. The device further includes a clamping or locking mechanism for holding the two mounting structures at a selected distance from each other once a gross alignment has been made, thus preventing them from responding further to a pushing or pulling force. The connector is joined to the radius mounting structure through a compound joint that allows the radius mounting structure to rotate freely yet independently about two rotational axes, and preferably only two, one of which is substantially parallel to the longitudinal axis of the radius, and the other is transverse to the first. The preferred angle between the two axes is within the range of about 83° to about 88°. Freedom of rotation around the second axis (which is transverse to the axis of the connector) is an effective means of achieving translational alignment of the bone fragments in the palmar-dorsal direction. Stabilization of the compound joint once the desired orientations are obtained is achieved by a locking mechanism that removes both rotational degrees of freedom either independently with separate locking components or simultaneously with a single locking action.

In embodiments that incorporate the incremental adjustments described above, these adjustments are performed using various means. The term "incremental adjustment" is used herein to mean a small adjustment, or adjustments that can be made in degrees or graduated stages, whose magnitude in either case can be closely controlled by the surgeon. Adjustments in the palmar-dorsal direction are preferably achieved by a gear such as a worm gear, adjustments in the proximal-distal direction are preferably achieved by a lead screw, and adjustments in the radial-ulnar direction are preferably achieved by a sliding connection along a minimal friction surface.

The present invention further lies in certain accessory features to an external fixator, which can be used in conjunction with some or all of the features cited above. One of these accessory features is a strain gauge for measuring and monitoring strain imposed on the patient's hand, wrist and forearm by the fixator along a direction parallel to the longitudinal axis of the radius. Another accessory feature is a motor and hinged drive shaft that produces a passive oscillating movement of the patient's wrist in flexion and extension while the fixator is in place. This feature reduces or eliminates the occurrence of complications that tend to arise when the tendons crossing the wrist and distal radius adhere to the surrounding soft tissue and bone. A third accessory feature is a spring-loaded distraction force component for attachment to the fixator to apply a continuous force pushing the metacarpal and radius mounting structures apart, thereby providing the fixator the additional capability of treating maluniting fractures of the radius (or partially healed radius fractures).

Further discoveries, features, advantages, and preferred embodiments of the invention will be apparent from the description that follows.

BRIEF DESCRIPTION OF THE DRAWINGS

FIG. 13 is a perspective view of an alternative stabilizing apparatus.

DETAILED DESCRIPTION OF THE INVENTION AND PREFERRED EMBODIMENTS

While the features and principles that characterize this invention and distinguish it over the prior art may be implemented in a variety of ways and embodied in a variety of constructions, these features and principles can best be understood by examination of specific examples. One such example is depicted in FIGS. 2 through 5 and another is shown in FIGS. 6 through 9.

Figure 2:
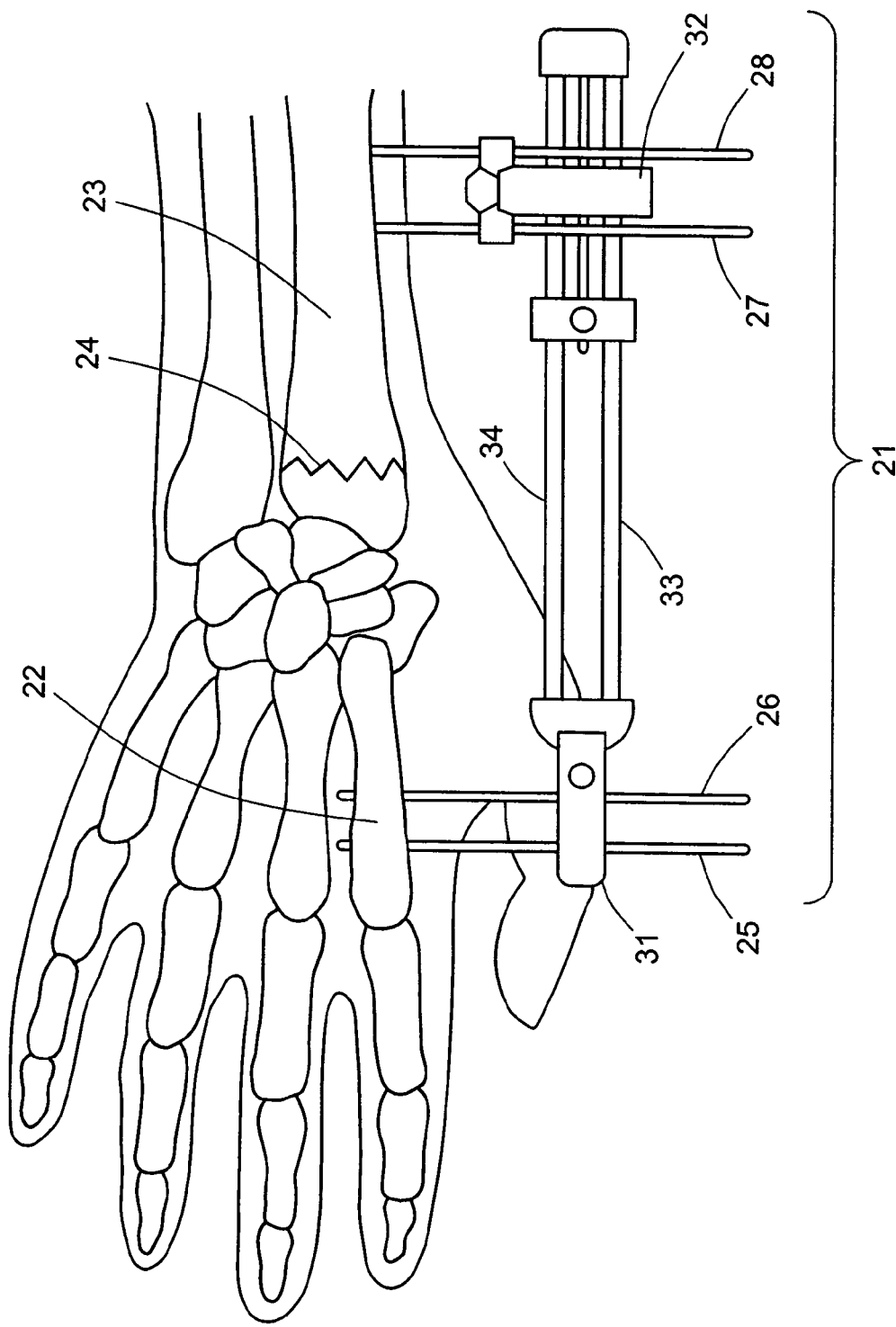
FIG. 2 is a plan view of an external fixator in accordance with this invention, in position on a forearm and hand that has suffered a Colles' fracture.

The view shown in FIG. 2 is that of the hand, wrist and distal end of the radius bone of a patient who has suffered a Colles' fracture, with an external fixator 21 in accordance with this invention applied to the fracture. The fixator is secured to the metacarpal 22 on the thumb side of the hand and to the radius 23 at a site proximal to the Colles' fracture site 24. While it may be appropriate or preferred in certain cases to secure the fixator to two or more metacarpals simultaneously, this example illustrates securement to only one metacarpal for purposes of clarity. Securement to the metacarpal is achieved in this example by a first pair of pins 25, 26 at the distal end of the fixator that are inserted into the metacarpal, while securement to the radius is achieved by a second pair of pins 27, 28 at the proximal end that are inserted into the radius. These pins can be replaced by screws or any other conventional means by which external fixators are applied. Two pins are shown for each end of the fixator, but this number may vary, provided that a stable and non-rotatable attachment is achieved. Ideally, the pins 25, 26, 27, 28 are coplanar with the stable finger metacarpals while the wrist is in a neutral position and the fracture is rotationally aligned by closed reduction, but the fixator can also function effectively when the two pins of the second pair are not coplanar with the finger metacarpals but are instead inserted at an angle relative to the metacarpal plane. Ideally, the two pins of the first pair 25, 26 are parallel to each other, as are the two pins of the second pair 27, 28. However, parallel placement of the two pins of each pair is not a requirement. The two pins of the first pair may or may not be parallel to the two pins of the second pair, depending on the technique used by the surgeon during insertion of the pins. As an optional feature, a drill guide may be used to insert the two pins of the second pair non-orthogonal to the longitudinal axis of the radius at a small angle to accommodate the truncated conical shape of the forearm. Fixators in which all four pins are parallel can also be used.

Each pair of pins is part of a mounting structure on the fixator. The mounting structure at the distal end of the fixator includes the metacarpal pins 25, 26 plus a metacarpal pin block 31 to which the metacarpal pins are secured. Likewise, the mounting structure at the proximal end includes the radius pins 27, 28 plus a radius pin block 32 to which the radius pins are secured. The metacarpal and radius pin blocks 31, 32 are joined by a connector, which in this example is a pair of parallel rails 33, 34, in a sliding connection that allows the distance between the pin blocks 31, 32 and hence the distance between the mounting structures to be shortened or lengthened. The parallel rails 33, 34 guide as well as limit the sliding motion of the pin blocks 31, 32 while preventing the blocks from rotating as they are being moved. This is a preferred feature of the present invention, since adjustments of the orientations of the pin blocks other than by shortening and lengthening the distance between them are preferably achieved by mechanisms within the pin blocks themselves, which are described below. Other types and shapes of connectors that similarly limit the sliding motion to a linear path of travel while preventing rotation can also be used. Examples are single non-circular rails, such as those of elliptical, square, or rectangular cross section, and tracks. Still others will be readily apparent to those skilled in the construction and use of external fixators.

Figure 3:
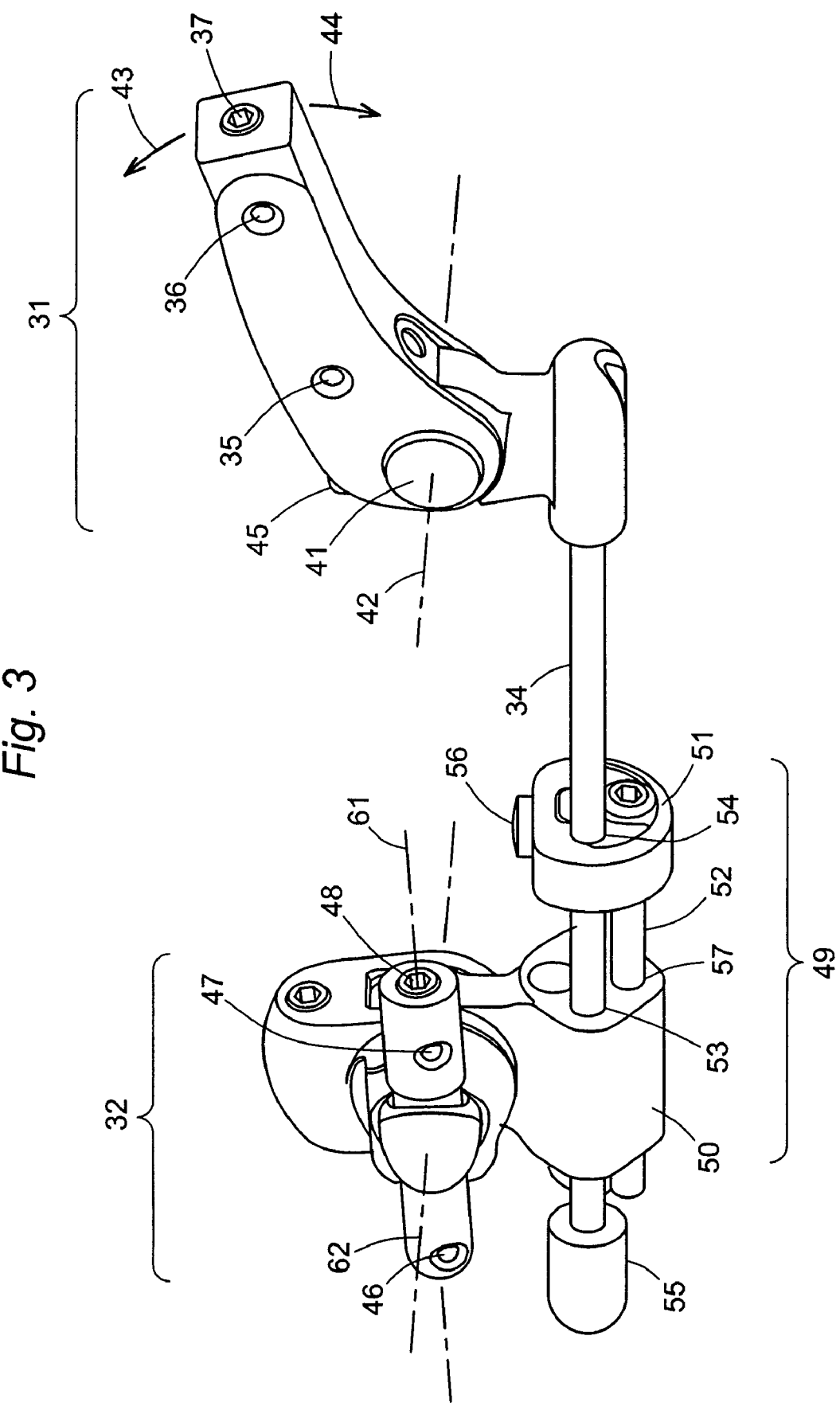
FIG. 3 is a perspective view of the external fixator of FIG. 2 viewed from the side facing the hand.

The pin blocks and rails are shown in perspective in FIG. 3. In this view, the pins have been removed and the remaining parts are shown from the side facing the patient's hand.

The metacarpal pin block 31 in FIG. 3 contains a pair of holes 35, 36 to receive the metacarpal pins 25, 26 (shown in FIG. 2), respectively. A set screw 37 oriented in a direction transverse to one of the holes 36 is tightened to lock both pins between a metacarpal pin spacer (which is positioned inside the pin block 31 between the two holes and therefore not visible in the Figure) and the pin holes and to thereby fix the position of the pin relative to the block. In alternative structures, the pins can be locked independently by separate set screws. Before the set screw 37 is tightened, the metacarpal pins 25, 26 can be moved back and forth within the metacarpal pin block 31, and this can be done even under a distraction load (tension applied in the proximal-distal direction) after the other adjustments have been made. By allowing the metacarpal pins to slide through the metacarpal pin block with minimal friction, the fixator permits the surgeon to move the hand, wrist, and distal fracture fragments in a radial-ulnar direction without allowing the fixator to freely rotate or translate in any other direction. The metacarpal pins and pin block can readily be made from materials that offer minimal sliding friction.

The metacarpal pin block in this example also contains a pivot joint 41 that permits rotation of the block around a transverse axis 42 that is perpendicular to the rails (only one of which, the inner rail 34, is visible) to describe an arc indicated by the arrows 43, 44. This arc corresponds to the direction of rotation of the flexion and extension of the patient's wrist. A set screw 45 presses against an internal member (not visible in this drawing) that fixes the block at a desired angle of rotation.

The radius pin block 32 likewise contains a pair of holes 46, 47 to receive the radius pins 27, 28 (of FIG. 2), respectively. A set screw 48 that is transverse to one of the holes 47 is tightened to lock both pins, forcing the pins against an internal pin spacer (internal to the pin block and not shown) and the sides of the holes. Here again, in an alternative arrangement the pins can be locked individually by independent set screws. Before the set screw 48 is tightened, the radius pins 27, 28 can be moved back and forth within the radius pin block 32, and, as in the case of the metacarpal pins, this can be done under a distraction load. This allows the fracture fragments to be moved in a radial-ulnar direction while the fixator is no longer able to rotate on the radius pins. To facilitate this back and forth movement of the radius pins relative to the radius pin block, the pins and pin block are constructed of materials that present minimal sliding friction.

Figure 1:
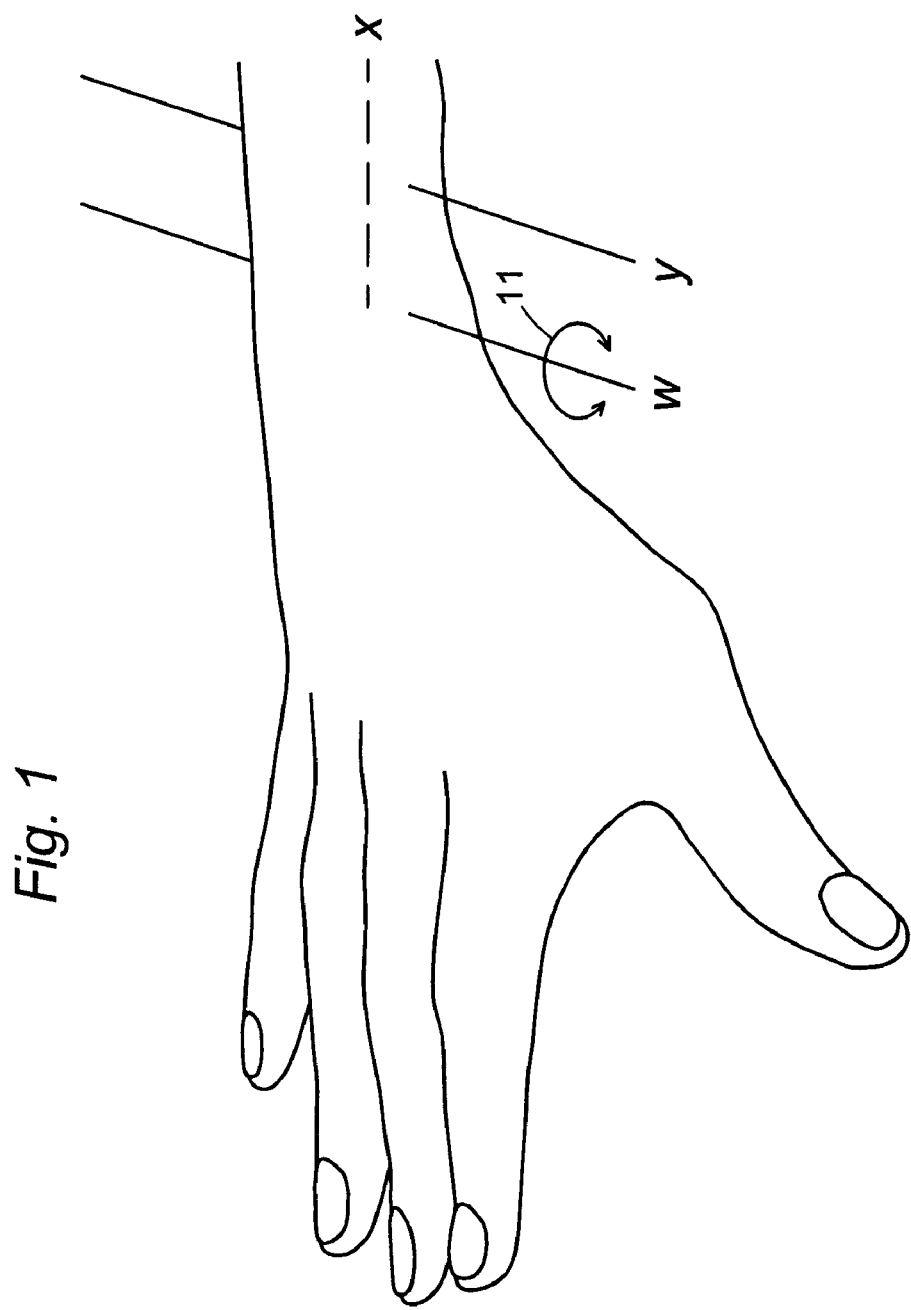
FIG. 1 is a perspective view of a forearm and hand illustrating the conventional set of orthogonal axes of the forearm, wrist, and hand.

The radius pin block is supported by a carriage 49 that travels over the connector rails. The carriage travels in the proximal-distal direction parallel to the x axis of FIG. 1, which is the longitudinal axis of the radius. The carriage is in two parts, a proximal part 50 and a distal part 51, that are joined by a threaded rod 52 which is part of a lead screw that is described further below. Each carriage part has a pair of bores 53, 54 through which the rails 33, 34 pass and which are large enough to allow the rails to slide through them with minimal friction that will allow the carriage to be moved by moderate manual force. The metacarpal pin block 31 in this example is bonded or otherwise immovably affixed to the distal ends of the rails so that only the radius pin block carriage 49 slides over the rails.

During the closed reduction procedure performed by the surgeon, the entire carriage 49 is free to slide along the rails, thereby altering the distance between the metacarpal pin block 31 and the radius pin block 32. A stop 55 is affixed to the rails at their proximal ends. The length of travel of the carriage 49 along the rails is limited in the proximal direction by the stop 55 and in the distal direction by the metacarpal pin block 31. Following the closed reduction alignment, the distance between the metacarpal and radius pin blocks is set and the carriage 49 is secured to the rails by a clamp screw 56 to prevent further sliding. The clamp screw 56 tightens a rail clamp inside the distal part 51 of the carriage, locking the carriage to the rails. For further adjustment of the distance, the threaded rod 52 is rotated through a drive nut 57 to move the proximal part 50 of the radius pin block 32.

The radius pin block 32 is of complex construction that permits the fixator to freely rotate about two axes and also provides geared movement. One axis 61 is parallel to the longitudinal axis of the radius, thereby permitting rotation of the fixator, and therefore the hand, wrist, and distal fracture fragments, relative to the proximal fragments of the radius about an axis parallel to the longitudinal axis of the radius. This axis 61 can itself be rotated about the second axis 62 which may intersect, and is generally perpendicular to, the first axis 61. In an alternative embodiment, the first axis 61 is not parallel to the radius, but is instead angled, or rotatable, to follow the truncated conical shape of the forearm. In the embodiment shown, rotation about the second axis of rotation 62 results in rotation of the fixator about an axis that is substantially perpendicular to the longitudinal axis of the radius. This second axis of rotation 62 is not itself movable, but is instead fixed and preferably perpendicular to the longitudinal axis of the rails.

Figure 4:
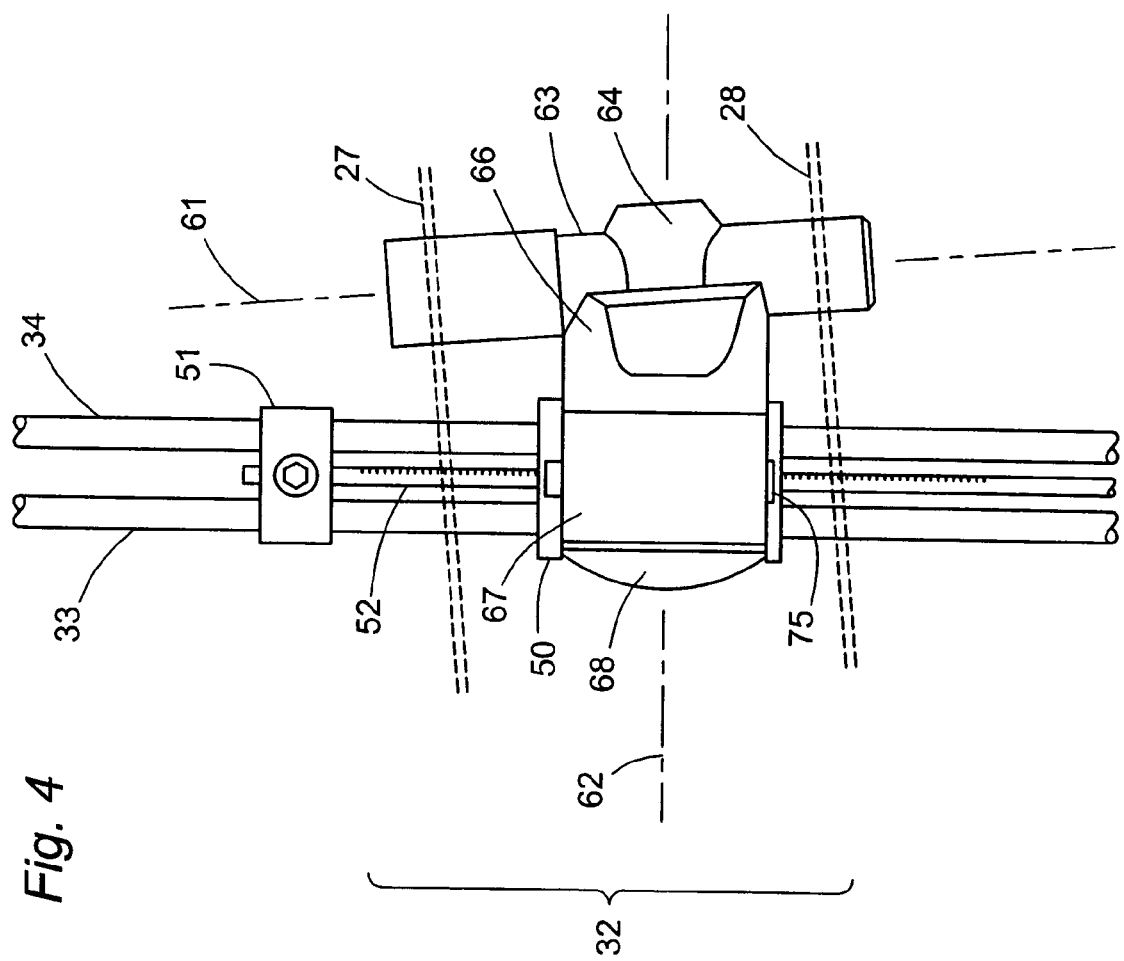
FIG. 4 is a plan view of the mounting structure by which the external fixator of the preceding Figures is attached to the radius bone.
Figure 5:
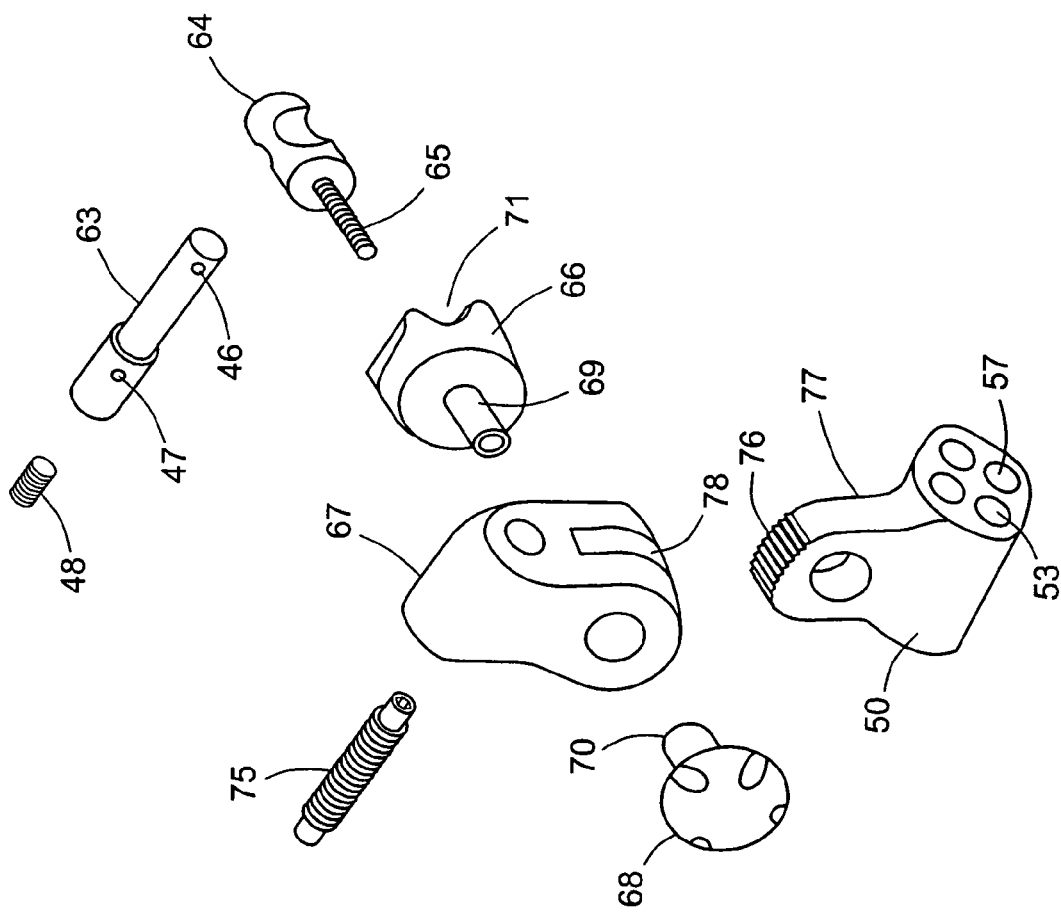
FIG. 5 is an exploded view in perspective of the mounting structure of FIG. 4.

FIG. 4 is an enlarged view of the radius pin block 32 with the radius pins 27, 28 and the connector rails 33, 34 depicted in position (the radius pins are shown in dashed lines), while FIG. 5 presents an exploded perspective view without the pins and rails. The component parts of the radius pin block are (a) a radius pin bar 63 which, together with the pins 27, 28, form the radius mounting structure, and (b) the compound joint which joins the radius pin bar to the connector rails 33, 34. The radius pins 27, 28 pass through holes 46, 47 in the radius pin bar 63 (shown in both FIGS. 4 and 5) whose axis is the first axis of rotation 61. As noted in the description of FIG. 3, the pins are rendered immovable in these holes by a set screw 48 in combination with an internal pin spacer (equivalent to those described above and not shown in the Figures).

The component parts of the compound joint are a bar housing or loop 64, a bar clamp housing 66, a central block 67, and a lock nut 68 which secures the bar loop, bar clamp housing, and central block to the proximal part 50 of the carriage. The pin bar 63 passes through the bar loop 64 which serves as a clamp for the pin bar 63 when forced against the pin bar. Extending from the loop 64 is a threaded axle 65 (FIG. 5) that passes through the bar clamp housing 66 and the central block 67 and is held in place by the lock nut 68. The bar clamp housing has a tubular extension 69 and the lock nut also has a tubular extension 70. The axle 65 passes through both of these extensions, the lock nut tubular extension 70 being threaded internally to mate with the threaded end of the axle 65. The bar clamp housing 66 has a transverse groove 71 on the end facing the loop 64. The groove 71 is of semi-circular cross section with a curvature complementary to that of the radius pin bar 63. Thus, when the bar 63 is inserted in the loop 64 and the axle 65 is loosely threaded into the lock nut tubular extension 70 with the bar clamp housing 66 and central block 67 in between, the bar 63 can rotate about its axis 61. Once the lock nut is tightened, the pin bar 63 is seized between the loop 64 and the groove 71 of the bar clamp housing and can no longer rotate about its axis 61.

By virtue of this construction, the compound joint is a single compound joint that provides a single means for simultaneously fixing the radius mounting structure at any rotational orientations that the surgeon chooses to select relative to both the first axis 61 and the second axis 62. The term "single" is used in conjunction with the compound joint to emphasize the fact that the joint secures the two parts (the radius mounting structure and the connector rails) together at a single location on each part while being capable of movement (and likewise permitting the two parts to move) in different directions. The terms "single" and "simultaneous" are also used in conjunction with the fixing means to emphasize the fact that only one tightening mechanism is needed for establishing fixed orientations about both axes.

The fixator is designed to be attached to the radial side of the hand and the radius bone, and the component parts shown in FIGS. 4 and 5 are assembled in an orientation intended specifically for the right hand and right radius. The same parts can be used for the left hand and left radius, simply by disassembling and reassembling the parts that are inserted into the central block 67 from the opposite side. That is, the pin bar 63, the pin bar loop 64, the bar clamp housing 66, and the lock nut 68 can be inserted into the central block 67 from the side opposite to that shown and thereby be ready for use on the left hand and left radius.

While the lock nut 68 is still loose, the bar clamp housing 66 is itself rotatable about the second axis of rotation 62 that passes through both tubular extensions 69, 70 and is coaxial with the axle 65. Tightening of the lock nut 68 causes the pin bar 63 to be seized by the bar clamp housing 66 and also causes the bar clamp housing 66 to be seized by the central block 67. The device is therefore locked simultaneously relative to both degrees of rotational freedom.

After the lock nut 68 has been tightened and the pin bar 63 and bar clamp housing 66 are both seized and no longer free to rotate about their respective axes, the radius pin block can still be rotated about the second axis of rotation 62 using a worm gear within the central block 67. As seen in FIG. 5, the worm gear includes a threaded shaft 75 whose threads engage a toothed curved edge 76 on the proximal carriage 50 that guides the travel of the components along the rails. The toothed curved edge 76 is the upper edge of an extension 77 of the proximal carriage 50, and the extension fits inside a slot 78 in the central block 67. The tubular extensions 69, 70 pass through openings in both the central block 67 and the extension 77 of the proximal carriage 50, thereby joining the central block to the carriage and allowing the central block to rotate relative to the carriage about the second (transverse) axis of rotation 62 (FIG. 4). The threaded shaft 75 is rotatable by appropriate means such as a hexagonal wrench (not shown). The rotation of the shaft 75 causes the proximal carriage 50 to rotate relative to the central block 67. This provides the incremental (i.e., precision or fine-tuning) adjustment of the fracture fragments in the palmar-dorsal direction.

The proximal carriage 50 and distal carriage 51 are connected by a lead screw 52 (FIGS. 3 and 4) that provides the incremental adjustment of the distance between the metacarpal and radius mounting structures. The lead screw 52 is mounted at one end to the distal carriage 51 and to a drive nut 57 (FIGS. 3 and 5) in the proximal carriage 50. Once the distal carriage 51 is secured to the rails by the clamp screw 56 (FIG. 3), the lead screw 52 is turned to cause the proximal carriage 50 to move toward or away from the distal carriage 51, which causes the radius pins in the radius pin block 32 to move toward or away from the metacarpal pins in the metacarpal pin block 31.

The threaded shaft and the lead screw can be designed for turning by a hexagonal wrench or any other equivalent means such as a knurled knob, finger tab, or the like. The same is true for each of the clamping screws shown in these Figures.

Returning to FIG. 3, the utility of the external fixator of this invention is enhanced by the position of the connector rails 33, 34 relative to the holes 35, 36, 46, 47 for the metacarpal and radius pins. The rails 33, 34 are offset from the plane of the holes (and hence the pins) in the palmar direction, leaving an open space between the two sets of pins. An offset in the palmar direction allows the surgeon unobstructed surgical exposure of the fracture site from both the palmar and dorsal directions, and especially from the radial aspect of the radius bone. This access offers the surgeon greater ease in performing any manipulations or surgical procedures (such as inserting pins, screws, or plates, or performing bone grafts) that are needed to optimally set the bone. The offset also allows the surgeon to take radiographic images of the fracture site without interference from any part of the fixator. To further add to the flexibility of the imaging process, the rails can be made of a radiolucent material, many of which are known in the art.

Figure 6:
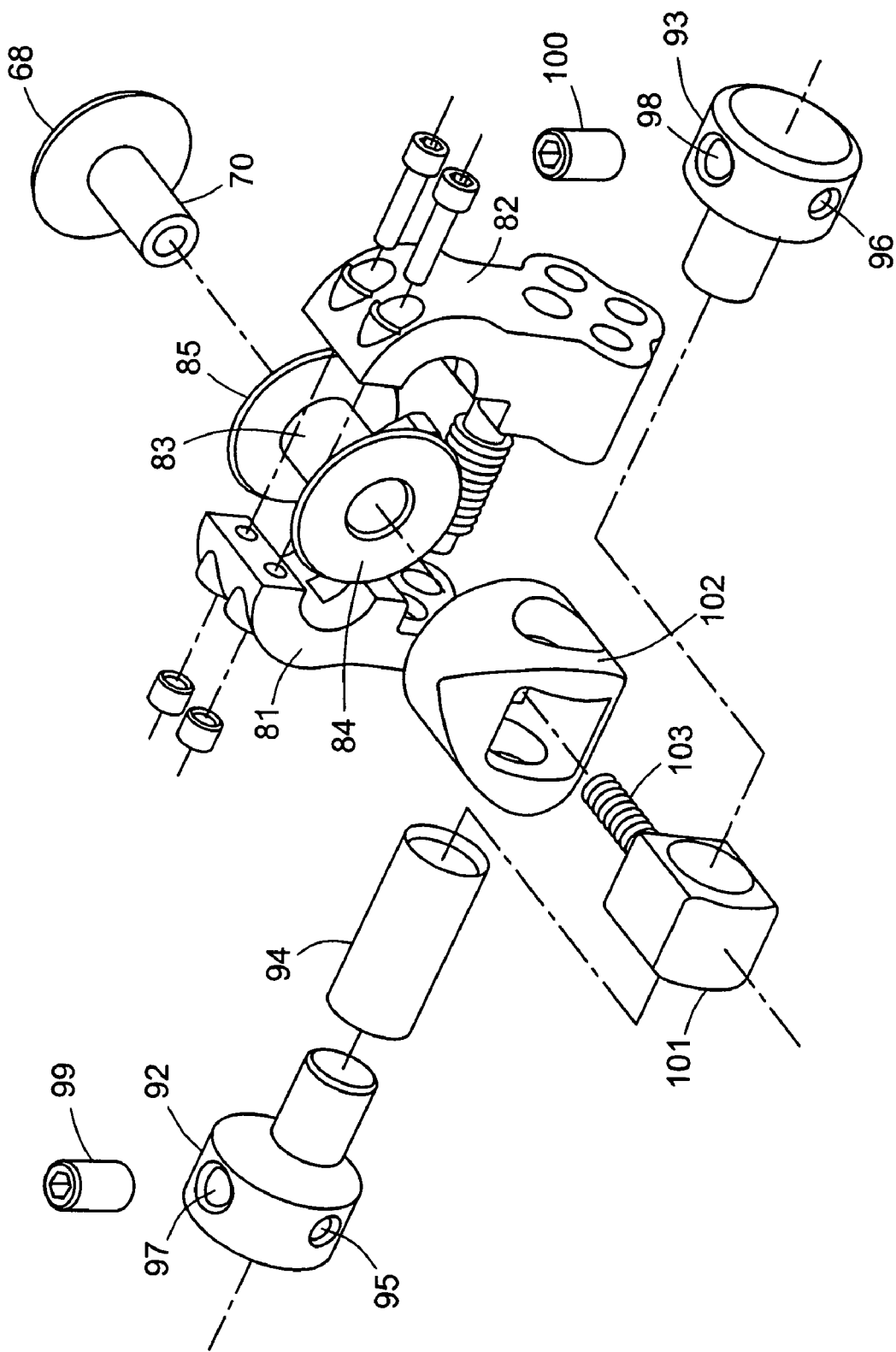
FIG. 6 is an exploded view in perspective of an alternative mounting structure by which the external fixator can be attached to the radius bone.
Figure 7:
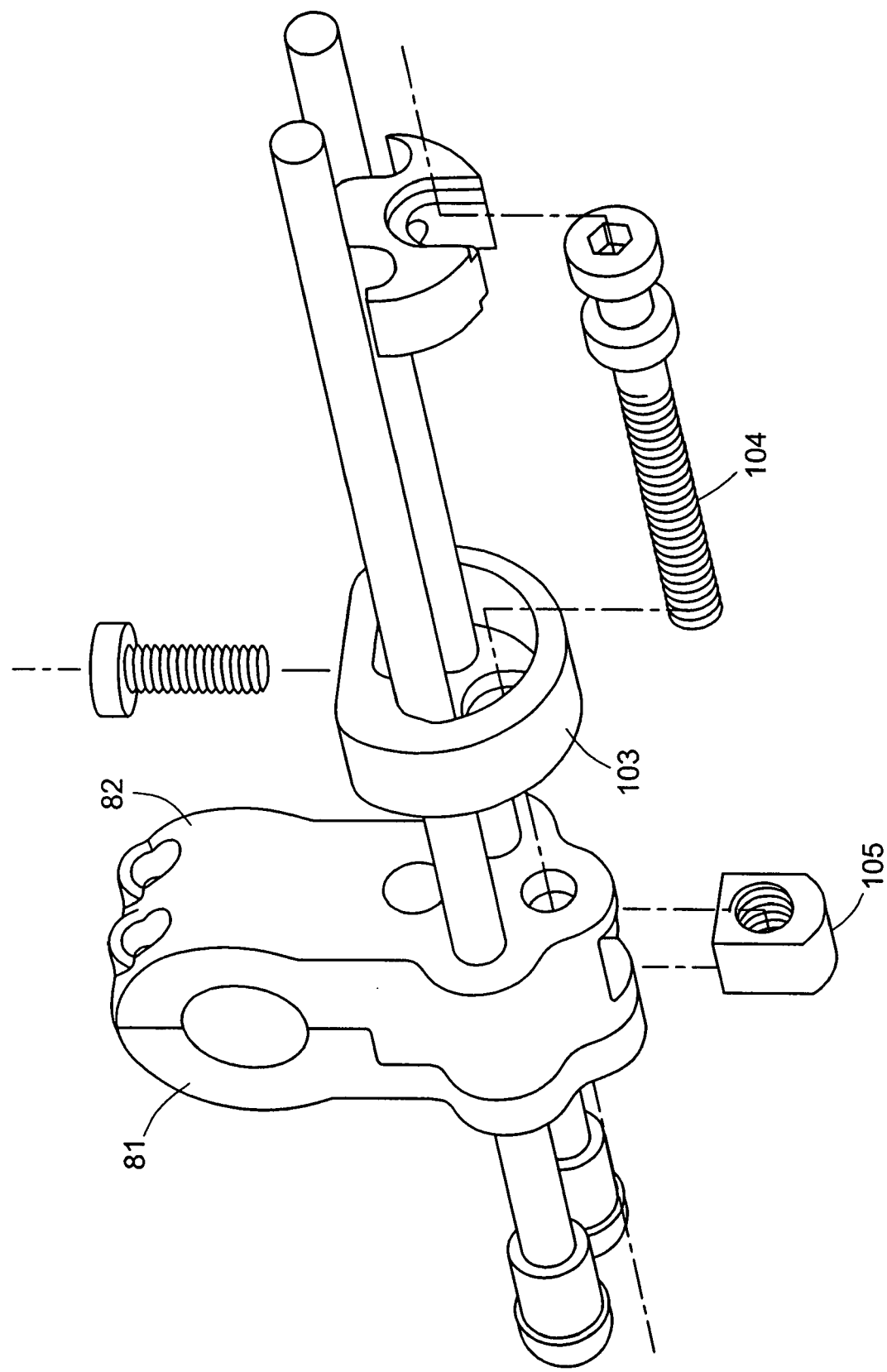
FIG. 7 is a partially assembled view of some of the component parts of the mounting structure of FIG. 6.
Figure 8:
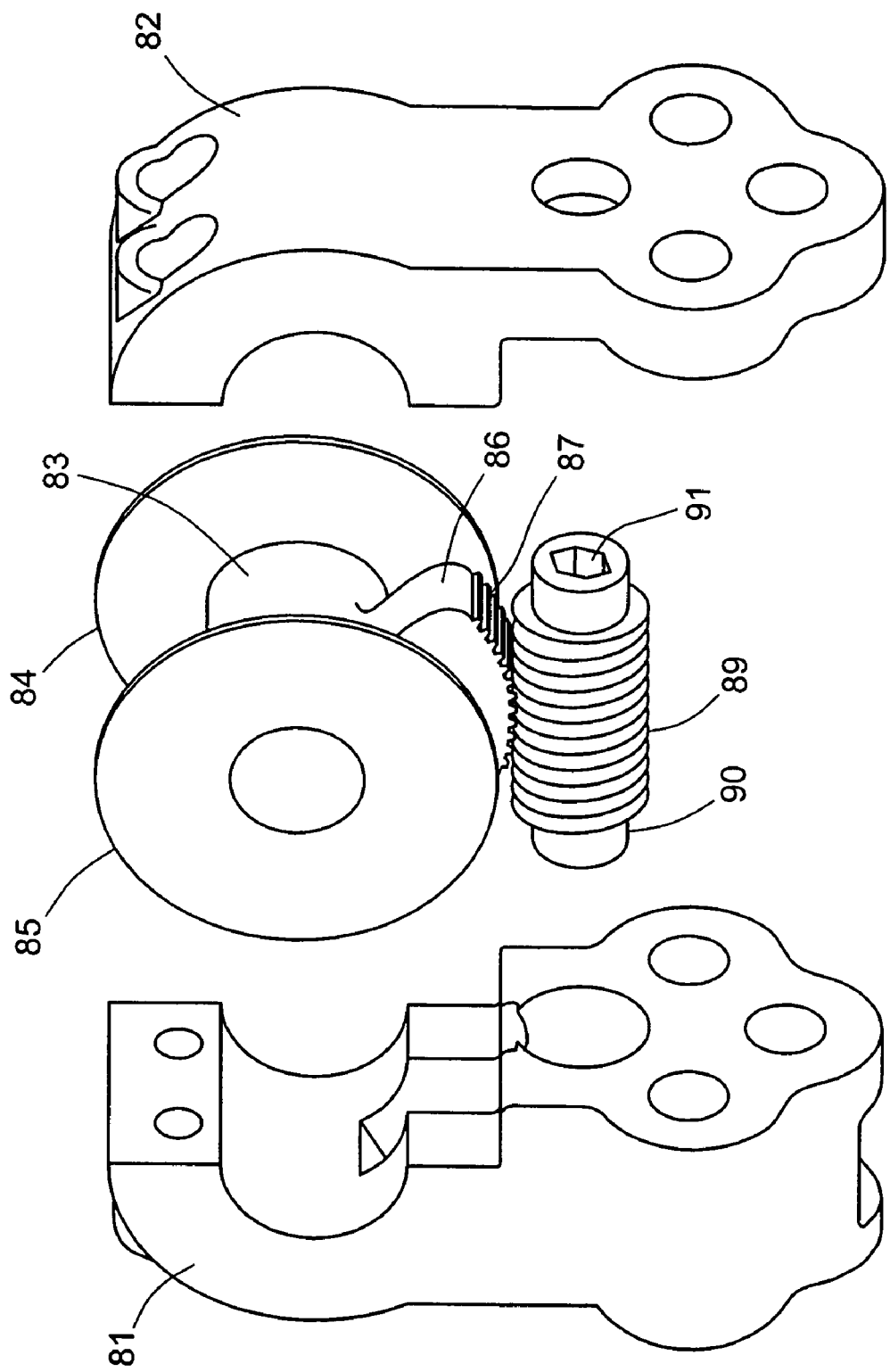
FIG. 8 is a still further view of some of the component parts of the mounting structure of FIG. 6.

An alternative, and preferred, construction for a radius pin block is shown in FIGS. 6, 7, and 8. This pin block can be substituted for the pin block in the FIGS. 3, 4, and 5 and used in combination with the metacarpal pin block, rails, and all other components of FIGS. 3, 4, and 5. In the construction shown in FIGS. 6, 7, and 8, the proximal carriage 50 and central block 67 of the construction in the preceding figures is replaced by a clamshell-type housing consisting of a proximal half 81 and a distal half 82 (FIG. 6) that when joined as shown in FIG. 7 encircle a hollow cylinder 83 (FIG. 6). The cylinder 83 terminates in flanges 84, 85 at its two ends, which hold the cylinder inside the clamshell. Extending downward from the cylinder 83 is a tab 86 (FIG. 8) with a toothed lower curved edge 87. The toothed edge 87 mates with threads 89 on a shaft 90, the shaft and toothed edge forming a worm gear by which the cylinder 83 is rotated. The worm gear is turned by any conventional means; in these Figures, the turning means is a hexagonal socket 91 at the end of the shaft 90 which is turned by a hexagonal wrench.

The radius pin bar 63 of FIG. 5 is replaced in the construction of FIG. 6 by a radius pin holder which consist of two knobs 92, 93 that are press fit into the two open ends of a cylinder 94. The knobs have through-holes 95, 96 through which the radius pins are inserted, and threaded holes 97, 98 into which set screws 99, 100 are inserted to fix the positions of the pins. The radius pin holder passes through a clamp loop 101 located inside a clamp housing 102. Extending from the clamp loop is a threaded axle 103 that mates with the tubular extension 70 on the lock nut 68, the tubular extension and lock nut being identical to those of the construction of FIG. 5. The radius pin holder is free to rotate about an axis equivalent to the axis 61 within the clamp loop 101 and clamp housing 102 until the lock nut 68 is tightened, which causes the clamp loop 101 to press the radius pin holder cylinder 94 against the clamp housing 102 and thereby fix the position of the radius pin holder. The radius pin holder is also free to rotate about an axis passing through the cylinder 83 which is equivalent to the axis 62 of the construction of FIG. 3. Tightening of the lock nut 68 stops this rotation as well, since it causes the clamp housing 102 to press against the flange 84 on the end of the cylinder.

As in the construction of FIG. 5, the two halves of the clamshell housing 81, 82 are joined to the distal carriage 103 (FIG. 7) by a lead screw 104 that mates with a drive nut 105 to provide incremental adjustment along the proximal-distal axis.

Figure 9:
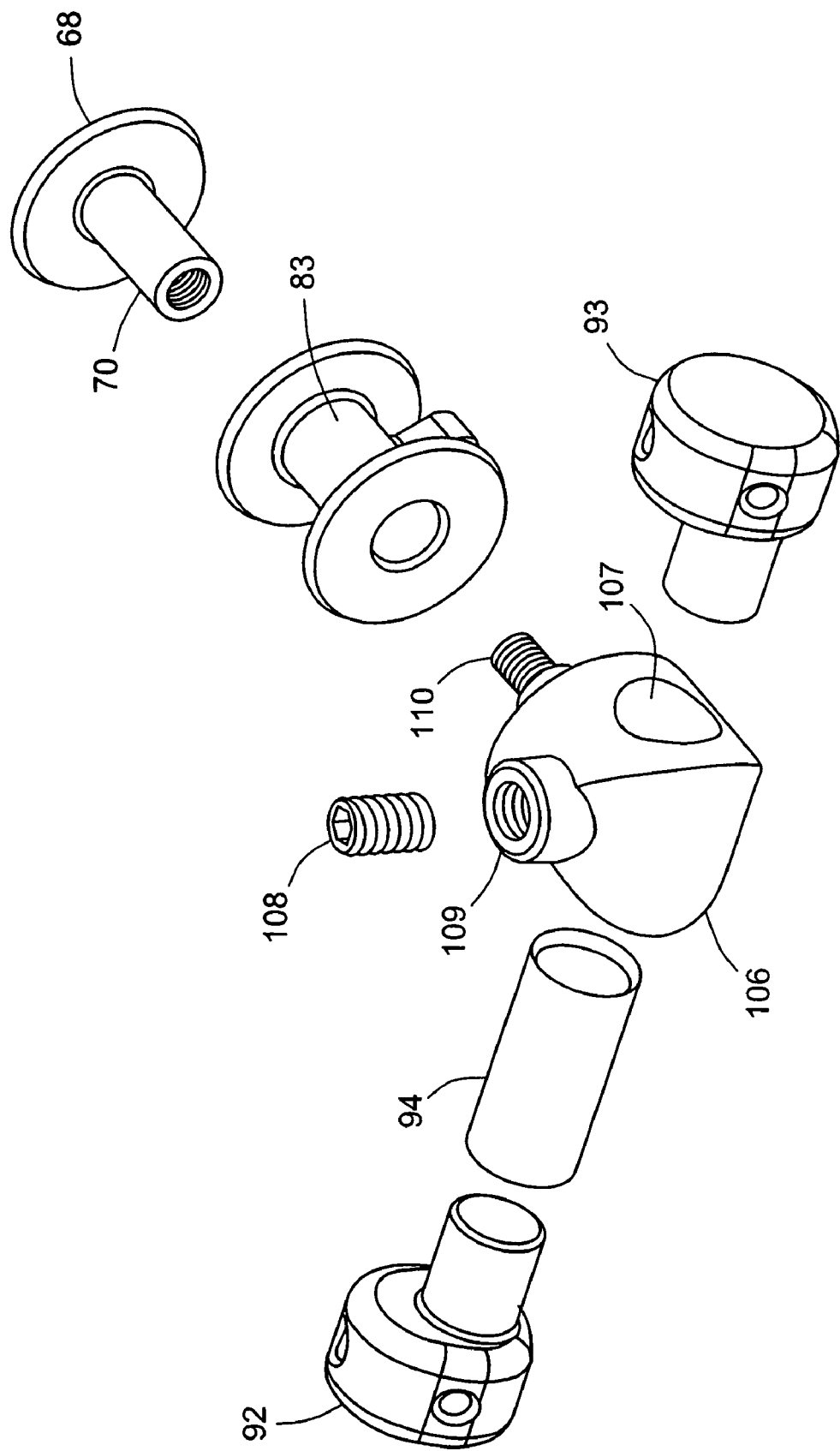
FIG. 9 is an exploded view in perspective of an alternative to some of the clamping components of the structure of FIG. 6.

FIG. 9 depicts an alternative to the construction shown in FIG. 6, in which the clamp loop 101 and clamp housing 102 of the FIG. 6 construction are replaced by an integrated clamping member 106 that has a through-passage 107 for the cylinder 94, and a clamp screw 108 that mates with a threaded boss 109 on the clamping member to engage the cylinder 94 and thereby fix the rotational position of the cylinder. The threaded axle 103 on the claim loop 101 of the FIG. 6 construction is replaced by a threaded axle 110 on the integrated clamping member which mates with the threaded tubular extension 70 on the lock nut 68. The construction of FIG. 9 permits the surgeon to fix the radius pin bar in each of its two rotational degrees of freedom independently, one rotational direction being fixed by the lock nut 68 and the other by the clamp screw 108.

Figure 10:
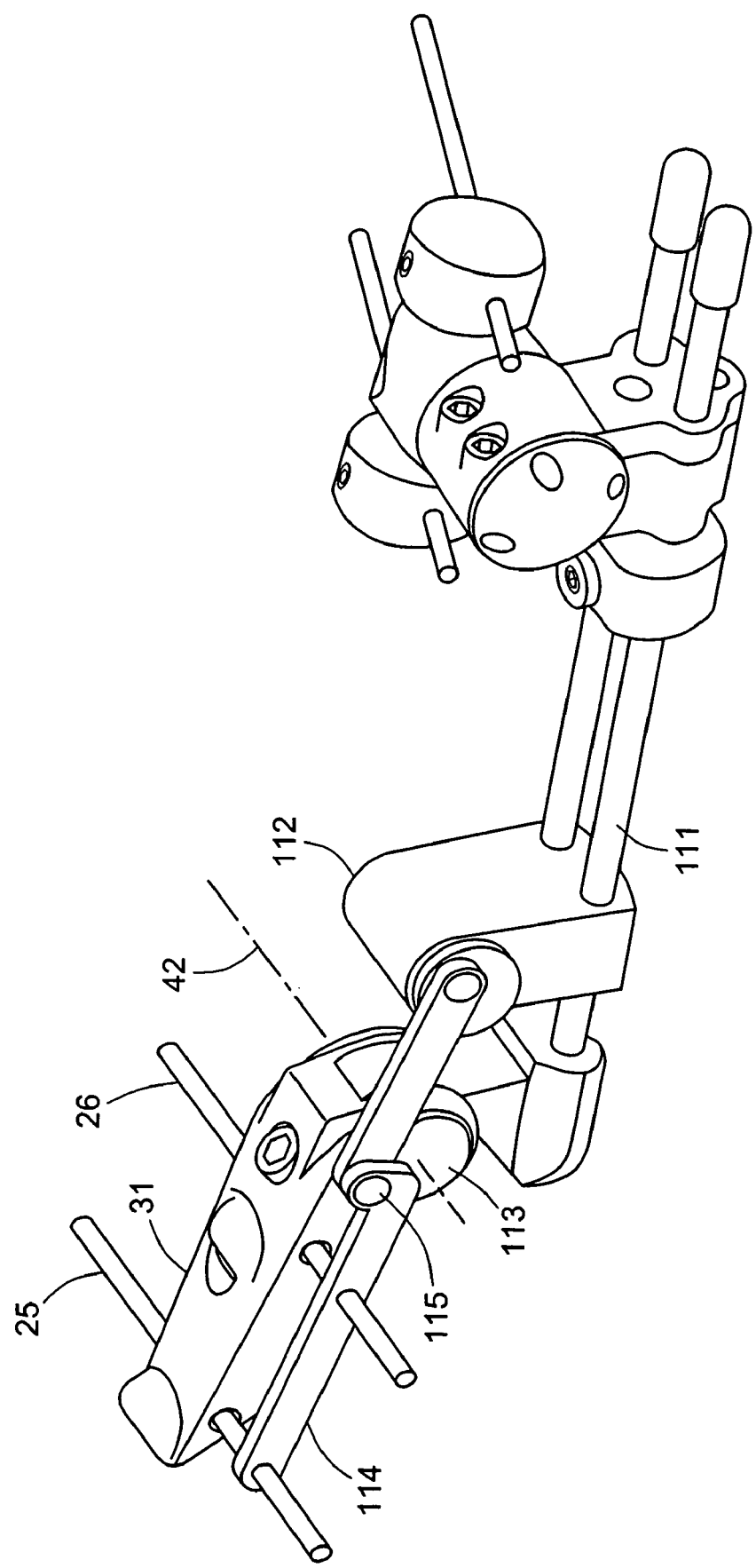
FIG. 10 is a perspective view of an assembled external fixator that incorporates the radius mounting structure of FIGS. 6, 7, and 8 and contains a strain gauge and a reciprocating motor as accessory features.

FIG. 10 depicts a fully assembled external fixator incorporating the radius mounting structure of FIGS. 6, 7, and 8 with additional optional features. The first of these optional features is a strain gauge 111 that is shown as being mounted to one of the rails 33. The strain gauge 111 is of conventional construction and is connected to conventional circuitry (not shown) for conditioning and monitoring the signal generated by the gauge. The strain gauge enables the surgeon to monitor the distraction load being applied to the soft tissues of the patient's hand, wrist and forearm by the fixator, and can be used in conjunction with the lead screw 52 of FIG. 3 or the lead screw 104 of FIG. 7, to alert the surgeon when excessive force is being applied. Examples of strain gauges that can be used in this invention are bondable foil strain gauges, available from Vishay Measurements Group, Malvern, Pa., USA.

The other optional feature shown in FIG. 10 is a rotary motor 112 that produces a reciprocating movement in a linkage 113 which is joined to the metacarpal mounting structure 31 through a second linkage 114, the two linkages joined by a hinge connection 115. The rotation of the motor 112 causes the first linkage 113 of the drive shaft to move back and forth. Since the second linkage 114 is attached to the metacarpal pins 25, 26, the back-and-forth motion of the first linkage 113 translates to a pivoting motion of the second linkage 114 and hence an oscillating pivotal motion of the metacarpal mounting structure 31 about its transverse axis 42. This produces a continuous or intermittent passive motion of the wrist of a patient to whom the device is mounted, whereby the patient's hand oscillates between flexion and extension while fracture alignment is maintained. This passive motion causes the tendons that cross the wrist to move while the fracture heals, thereby preventing complications arising from adherence of the tendons to the surrounding soft tissue and bone. The motor is a conventional rotary motor that can be driven by a conventional power source such as a battery. Suitable motors, electric controllers, and batteries are readily available from commercial suppliers.

Figure 11:
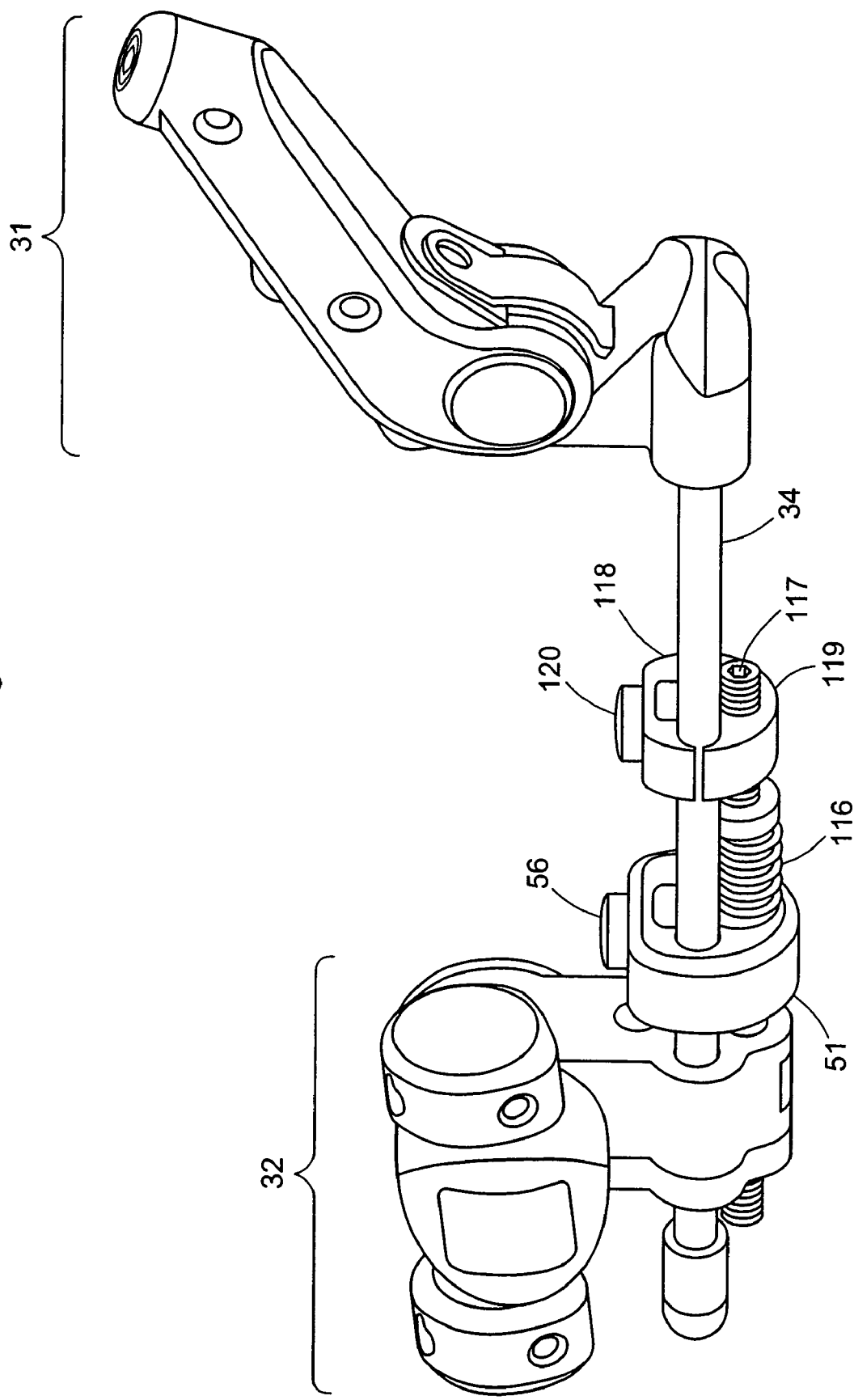
FIG. 11 is a perspective view of an external fixator in accordance with the invention with an added feature for applying a distraction force in a highly controlled manner.

An added feature that is included in certain fixators of the present invention and that will be useful in treating certain conditions is shown in FIG. 11. This feature is a compression spring that applies an elongating force pushing the metacarpal mounting structure 31 and the radius mounting structure 32 apart from each other. In the example shown in this Figure, the component is a coil spring 116, a spring adjustment screw 117, and a rail clamp that has an upper section 118, a lower section 119, and a clamp screw 120. Also shown in the Figure are components of the fixator that are also shown in the preceding Figures, notably the rails 34, the distal carriage 51 and the carriage clamp screw 56 that fixes the position of the distal carriage 51 on the rails 34.

One of the conditions that the construction of FIG. 11 is designed to treat is a maluniting fracture, which occurs when radius fracture fragments collapse as the fracture is healing, thereby shortening the radius bone. This condition is detectable by x-ray, and the primary option currently available to the surgeon for correcting a malunion is to wait until the bone finishes healing, make a surgical cut in the radius bone, and add a bone graft to restore the radius to its proper length. Another condition that the construction of FIG. 11 can be used to treat is an abnormally short radius bone that requires lengthening.

To apply the construction of FIG. 11 to either of these conditions, the fixator is secured to the metacarpals and the radius by the methods described above in conjunction with the preceding Figures, and the clamp screw 120 is tightened to clamp the rails 34 between the two sections 118, 119 of the rail clamp. With the proximal end of the spring 116 pushing against the distal carriage 51, the carriage clamp screw 56 is loosened, causing the entire carriage to be free to slide. In the case of either a maluniting radius, the radius (whether partially healed from a fracture or intact but short) limits the sliding of the carriage, and the spring 116 applies a distraction force (i.e., an elongating tension) to the radius. The spring adjustment screw 117 is joined to the distal end of the spring 116 and the compression of the spring, and hence the distraction force, are adjusted by turning this adjustment screw. This adjustment permits the surgeon to select the distraction force that is most appropriate for any particular patient.

While a distraction force is already applied by the fixator constructions without the elongating tension component shown in FIG. 11, one feature added by the inclusion of the elongating tension component is greater control of the distraction force. Another feature is a continuing distraction force as the radius lengthens in response to the force. While the force will lessen as lengthening radius lowers the compression on the spring, a force will remain present although of proportionally lesser magnitude. If desired, the original force can be restored by appropriate adjustment of the spring adjustment screw 117 to re-compress the spring 116.

Figure 12:
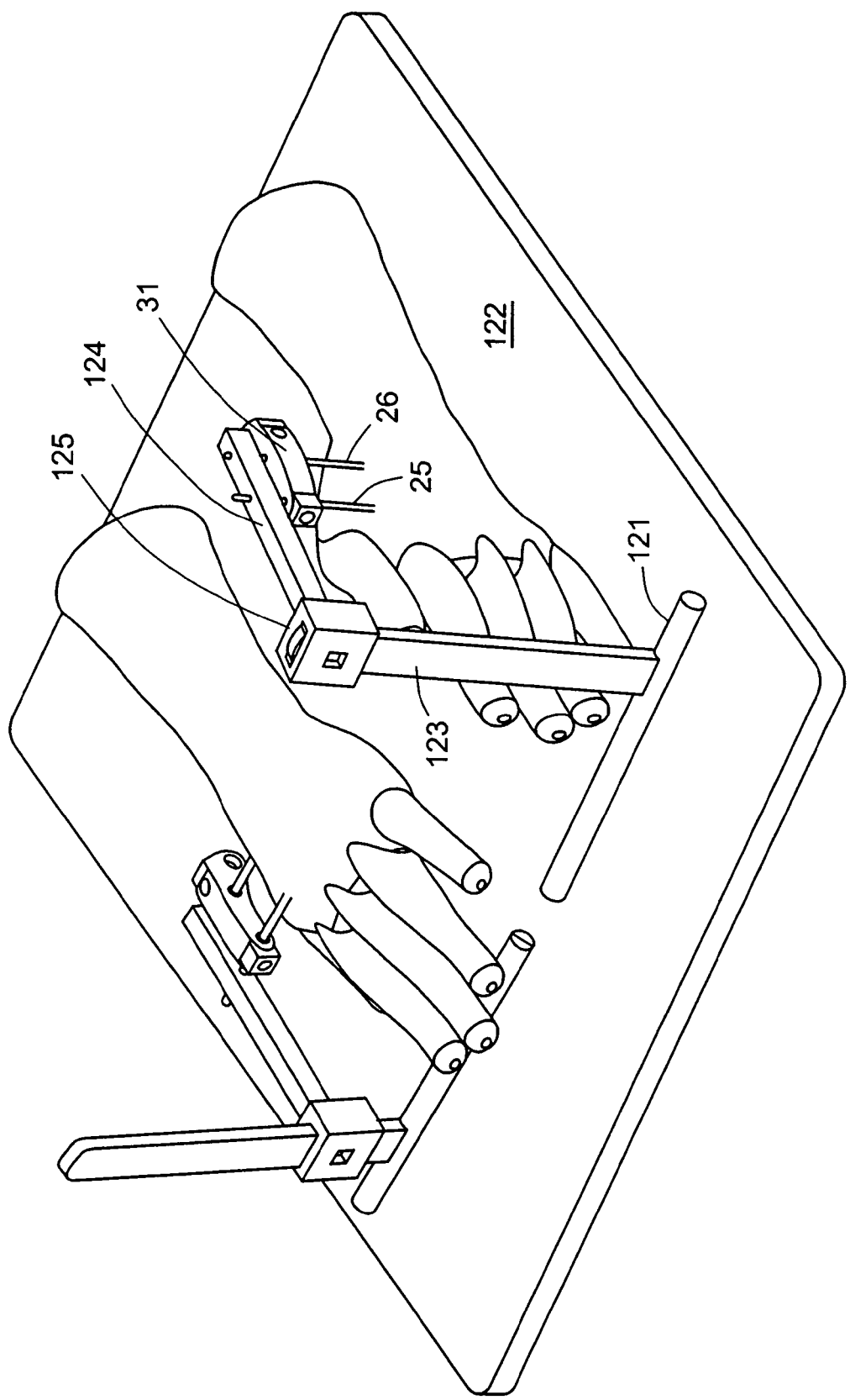
FIG. 12 is a perspective view of a stabilizing apparatus for holding the external fixator of the preceding figures steady during radiographic examination of the fracture site.

The external fixator can be stabilized on an x-ray or operating room table to hold the hand in a fixed position while x-ray images are taken, and to allow the surgeon to manipulate the bones and make the various adjustments while viewing the images, or simply to perform the manipulations and adjustments without movement of the hand or forearm. One example of a stabilizing structure is shown in FIG. 12. The structure has a base bar 121 that rests on the table 122, and a post 123 extending vertically from the base bar. A beam 124 is attached to the post 123 through a sliding joint 125, and the beam 124 has apertures to receive the exposed ends of the metacarpal pins 25, 26. The beam 124 can be mounted in either of two orientations to allow x-ray images to be taken in two orthogonal planes. The orientation on the left is the anterior-posterior orientation with the plane of the hand parallel to the surface of the table, while in the orientation on the right is the lateral orientation in which the hand is turned upward so that its plane is vertical.

A second example of a stabilizing structure is shown in FIG. 13. This structure is a series of hinged plates 131, 132, 133 with a beam 134 mounted to one of the plates 133 through a pivot connection 135. The hinges 140, 141 joining these plates allow the structure to be raised to different heights to accommodate differences in the sizes of the hands and forearms of different patients. The beam has two apertures 136, 137 to receive the exposed ends of the metacarpal pins 25, 26. To stabilize the patient's forearm and fixator for radiographic imaging, the beam apertures 136, 137 are slid over the pins 25, 26, and the forearm and fixator are manipulated by the surgeon, x-ray technician, or radiologist to the desired position. The end plate 131 is placed flat on the x-ray table surface and held in place with a weight or a weighted piece of equipment, or otherwise clamped to the table. The pivot connection 135 allows the stabilizer to be used on either the left hand and forearm or the right hand and forearm, and also allows the stabilizer to hold the hand in the anterior-posterior position or the lateral position, or at any angle in between these two positions.

External fixators in accordance with this invention can be applied and used in a variety of ways, and the various adjustments and alignments can be performed in different sequences. Utilizing the fixator shown in FIGS. 2 through 5, for example, the surgeon begins by inserting the pins into the appropriate locations in the metacarpal(s) and the radius before the pins have been inserted into their respective pin blocks. The metacarpal pin block 31 and the proximal carrier 50 will already have been mounted to the rails, while the lock nut 68 and the radius pin clamp components, which consist of the pin bar 63 (including the set screw 48 and the internal pin spacer), the loop 64, and the bar clamp housing 66, are separated from the remainder of the radius pin block. The pin bar 63, loop 64, and housing 66 are assembled, slipped over the radius pins and tightened against the pins with the set screw 48. Excess lengths of the radius pins that protrude from the pin bar can be cut off to prevent interference with the central block 67 as the fixator rotates about the axis 62. The pins and clamping components are then joined to the remaining parts of the radius pin block, which are already mounted to the rails.

Depending on whether the fractured radius is on the left or right forearm, the pin bar 63, loop 64, and housing 66 can be inserted through either side of the central block 67, and the lock nut 68 is loosely attached to the axle 65 so the radius pin clamp assembly is free to rotate about both axes 61 and 62 (FIG. 4). Simultaneously, the metacarpal pin block 31 is slid over the metacarpal pins 25, 26 (FIG. 2) which remain free to slide through the holes 35, 36 (FIG. 3). With the carriage clamp screw 56 (FIG. 3) loose, the radius pin block 32 can move freely back and forth relative to the metacarpal mounting structure 31. The surgeon then performs closed reduction by manually manipulating the forearm and hand. By placing a thumb or finger on the stop 55 and another finger on the distal end of the proximal carriage 50, the surgeon can control the distraction force applied to the fracture while receiving a tactile sense of the amount of force being applied. This is a valuable means of controlling the distraction force. During the closed reduction, the radius pin block 32 is free to rotate about both axes 61 and 62 and the carriage 49 is free to translate along the rails without constraining the movement of the fracture fragments. The clamp screw 56 and lock nut 68 (FIG. 5) are then tightened to eliminate free movement of the fixator and the incremental adjustments are made by either the worm gear for the palmar-dorsal alignment or the lead screw for the proximal-distal alignment, or by sliding the metacarpal pins 25, 26 through the metacarpal pin block for radial-ulnar alignment. Wrist flexion-extension adjustment can be made at any time during the procedure by rotation of the metacarpal pin block 31 and by tightening the corresponding set screw 45.

An analogous procedure can be used with the fixator of FIGS. 6, 7, and 8. Regardless of which fixator is used, the sequence described above is only an example. Other sequences will be readily apparent to the skilled surgeon.

The foregoing descriptions are offered for purposes of illustration. Modifications and substitutions of the various elements, their configurations and means of connection and movement, which also fall within the scope of the invention, will be apparent to those skilled in the art upon reading these descriptions.

What is claimed is:

1. An external fixation device for applying elongating tension between a radius that has been fractured at a distal fracture site and a metacarpal and for aligning fragments of said radius that have been displaced by said fracture, said device comprising:
   a metacarpal mounting structure capable of being affixed to said metacarpal;
   a radius mounting structure and means for affixing said radius mounting structure to said radius at a location proximal to said fracture site;
   a connector joining said metacarpal and radius mounting structures, said connector defining a connector axis and comprising means for moving said mounting structures relative to each other along said connector axis and means for fixing said mounting structures at a selected displacement along said connector axis; and
   a single compound joint joining said radius mounting structure to said connector, said single compound joint comprising means for allowing said radius mounting structure to rotate freely and independently about first and second rotational axes, and only about said first and second rotational axes, said second rotational axis being transverse to said first rotational axis, said single compound joint further comprising means for eliminating free rotation of said radius mounting structure about said first and second rotational axes by a single tightening step, said means for allowing said radius mounting structure to rotate and said means for eliminating free rotation being independent of said means for affixing said radius mounting structure to said radius.

2. An external fixation device in accordance with claim 1 in which said first rotational axis is substantially perpendicular to said connector axis.

3. An external fixation device in accordance with claim 1 further comprising means for adjusting the rotational orientation of said radius mounting structure about said first rotational axis while free rotation about said first and second rotational axes is eliminated by said means for eliminating free rotation.

4. An external fixation device in accordance with claim 3 in which said means for adjusting the rotational orientation of said radius mounting structure permits adjustment about said first rotational axis while maintaining a constant rotational orientation about said second rotational axis.

5. An external fixation device in accordance with claim 1 in which said connector comprises a beam to which one of said metacarpal and radius mounting structures is slidably but non-rotationally mounted, and said means for fixing said mounting structures at a selected displacement along said connector axis comprises (i) means for preventing sliding of said slidably mounted mounting structure along said connector axis by seizing said beam and (ii) a lead screw operable independently of said means for preventing sliding.

6. An external fixation device in accordance with claim 1 in which said metacarpal mounting structure comprises two metacarpal pins for insertion into said metacarpal and said radius mounting structure comprises two radius pins for insertion into said radius.

7. An external fixation device in accordance with claim 6 in which said metacarpal mounting structure further comprises a metacarpal pin block into which said metacarpal pins are slidably inserted, thereby permitting adjustment of said metacarpal pins relative to said metacarpal pin block independently of said means for fixing said mounting structures at a selected displacement along said connector axis.

8. An external fixation device in accordance with claim 6 in which said radius mounting structure further comprises a radius pin block into which said radius pins are slidably inserted, thereby permitting adjustment of said radius pins relative to said radius pin block independently of said means for fixing said mounting structures at a selected displacement along said connector axis.

9. An external fixation device in accordance with claim 6 in which said metacarpal mounting structure further comprises a metacarpal pin block into which said metacarpal pins are slidably inserted, and said radius mounting structure further comprises a radius pin block into which said radius pins are slidably inserted, thereby permitting adjustment of said metacarpal pins and said radius pins independently of each other relative to said external fixation device and independently of said means for fixing said mounting structures at a selected displacement along said connector axis.

10. An external fixation device in accordance with claim 1 in which said connector comprises a beam to which one of said metacarpal and radius mounting structures is slidably but non-rotationally mounted, said beam being sufficiently offset from both said rotational axes that when said external fixation device is mounted to a patient, access to said fracture site for surgical intervention is provided.

11. An external fixation device for applying elongating tension between a radius that has been fractured at a distal fracture site and a metacarpal and for aligning fragments of said radius that have been displaced by said fracture, said device comprising:
   a metacarpal mounting structure capable of being affixed to said metacarpal;
   a radius mounting structure and means for affixing said radius mounting structure to said radius at a location proximal to said fracture site;

a connector joining said metacarpal and radius mounting structures, said connector defining a connector axis and comprising means for moving said mounting structures relative to each other along said connector axis and means for fixing said mounting structures at a selected displacement along said connector axis; and a single compound joint joining said radius mounting structure to said connector, said single compound joint comprising means for allowing said radius mounting structure to rotate freely and independently about first and second rotational axes, and only about said first and second rotational axes, said second rotational axis being transverse to said first rotational axis, said single compound joint further comprising (i) means for eliminating free rotation of said radius mounting structure about said first and second rotational axes by a single seizing step and (ii) worm gear for adjusting the rotational orientation of said radius mounting structure about said first rotational axis while seized by said means for eliminating free rotation, said means for allowing said radius mounting structure to rotate, said means for eliminating free rotation and said worm gear being independent of said means for affixing said radius mounting structure to said radius.

12. An external fixation device for applying elongating tension between a radius that has been fractured at a distal fracture site and a metacarpal and for aligning fragments of said radius that have been displaced by said fracture, said device comprising:

a metacarpal mounting structure capable of being affixed to said metacarpal:

a radius mounting structure and means for affixing said radius mounting structure to said radius at a location proximal to said fracture site;

a connector joining said metacarpal and radius mounting structures, said connector defining a connector axis and comprising means for moving said mounting structures relative to each other along said connector axis and means for fixing said mounting structures at a selected displacement along said connector axis; and a single compound joint joining said radius mounting structure to said connector, said single compound joint comprising means for allowing said radius mounting structure to rotate freely and independently about first and second rotational axes, and only about said first and second rotational axes, said second rotational axis being transverse to said first rotational axis, said single compound joint further comprising (i) a means for eliminating free rotation of said radius mounting structure about said first and second rotational axes by a single seizing step and (ii) rotational adjustment means for adjusting the rotational orientation of said radius mounting structure about said first rotational axis while seized by said means for eliminating free rotation, said means for allowing said radius mounting structure to rotate, said means for eliminating free rotation and said means for adjusting the rotational orientation being independent of said means for affixing said radius mounting structure to said radius.

13. An external fixation device in accordance with claim 12 in which said single for eliminating free rotation is a single screw-operated tightener.

* * * * *